United States Patent [19]

Rains et al.

[11] Patent Number: 5,425,528
[45] Date of Patent: Jun. 20, 1995

[54] FLUID DISPENSING APPARATUS

[75] Inventors: John R. Rains, Dalhart; John Kittoe, Grand Prairie, both of Tex.

[73] Assignee: Vetrisystems, Inc., Dalhart, Tex.

[21] Appl. No.: 190,222

[22] Filed: Feb. 1, 1994

Related U.S. Application Data

[60] Continuation of Ser. No. 987,118, Dec. 8, 1992, which is a division of Ser. No. 779,268, Oct. 18, 1991, Pat. No. 5,188,610.

[51] Int. Cl.⁶ ............................................. F16L 37/28
[52] U.S. Cl. ............................. 251/149.1; 251/149.5; 604/905
[58] Field of Search ................... 251/149.5, 149.1; 285/396; 604/905

[56] References Cited

U.S. PATENT DOCUMENTS

| | | |
|---|---|---|
| 1,615,873 | 2/1927 | Fitch . |
| 1,619,120 | 3/1927 | Heaton . |
| 1,968,075 | 7/1934 | Ewald ........................ 251/149.5 |
| 2,074,401 | 3/1937 | Kauzal . |
| 2,793,073 | 5/1957 | Bateman . |
| 3,682,175 | 8/1972 | Halter . |
| 3,799,453 | 3/1974 | Hart ........................... 285/396 |
| 3,922,099 | 11/1975 | Christine et al. . |
| 3,930,761 | 1/1976 | Barraclough . |
| 3,986,508 | 10/1976 | Barrington . |
| 4,033,346 | 7/1977 | Phillips et al. . |
| 4,049,033 | 9/1977 | Ralston, Jr. . |
| 4,051,852 | 10/1977 | Villari . |
| 4,090,541 | 5/1978 | Cammarata, III et al. . |
| 4,201,406 | 5/1980 | Dennehey et al. . |
| 4,261,359 | 4/1981 | Chein . |
| 4,307,766 | 12/1981 | Tanokura . |
| 4,308,904 | 1/1982 | Martin et al. . |
| 4,319,699 | 3/1982 | Willers et al. . |
| 4,375,864 | 3/1983 | Savage . |
| 4,417,890 | 11/1983 | Dennehey et al. . |
| 4,526,298 | 7/1985 | Boxer et al. . |
| 4,588,402 | 5/1986 | Igari et al. . |
| 4,636,204 | 1/1987 | Christopherson et al. . |
| 4,723,687 | 2/1988 | Kutterer . |
| 4,836,416 | 6/1989 | Shalgi et al. . |
| 4,848,660 | 7/1989 | O'Connell . |
| 4,895,565 | 1/1990 | Hillstead ..................... 251/149.1 |
| 4,904,243 | 2/1990 | Bruera . |
| 4,969,883 | 11/1990 | Gilbert et al. ................. 604/905 |
| 4,981,469 | 1/1991 | Whitehouse et al. . |
| 5,009,391 | 4/1991 | Steigerwald ................. 251/149.1 |
| 5,037,399 | 8/1991 | Reichert et al. . |
| 5,059,182 | 10/1991 | Laing . |
| 5,064,416 | 11/1991 | Newgard et al. ............. 251/149.1 |
| 5,071,413 | 12/1991 | Utterberg ..................... 604/905 |
| 5,115,947 | 5/1992 | McDonnell et al. . |
| 5,139,488 | 8/1992 | Klein . |

FOREIGN PATENT DOCUMENTS

| | | |
|---|---|---|
| 14463 | of 1929 | Australia . |
| 22557 | 8/1930 | Australia . |
| 100290 | 2/1937 | Australia . |
| 108012 | 7/1939 | Australia . |
| 144297 | 11/1951 | Australia ..................... 251/149.5 |
| 2150814 | 7/1985 | United Kingdom . |

*Primary Examiner*—A. Michael Chambers
*Attorney, Agent, or Firm*—Randall C. Brown

[57] ABSTRACT

A fluid dispensing apparatus is provided which comprises a flexible, collapsible fluid container in fluid communication with an adjustable volume multi-dose dispensing means.

6 Claims, 2 Drawing Sheets

1

FLUID DISPENSING APPARATUS

This is a continuation of copending application(s) Ser. No. 07/987,118 filed on Dec. 8, 1992 which is a divisional of Ser. No. 07/779,268 filed Oct. 18, 1991, now U.S. Pat. No. 5,188,610.

BACKGROUND OF THE INVENTION

1. Field of the Invention

The present invention relates to apparatus for dispensing fluids. More particularly, the present invention relates to a portable apparatus for oral or parenteral adjustable volume, multi-dose administration of fluids such as medications, vitamins, nutrients, and other remedial or preventive compositions.

2. Description of the Prior Art

A conventional method for inoculating or orally force medicating livestock involves the use of a semi-rigid plastic container that serves as a reservoir for liquid medication. The container typically contains up to approximately three quarts of hand mixed or pre-mixed medication. The medication is poured into the container and capped with a lid having a flexible plastic hose attachment. The container is inverted and strapped to a user's back. The medication is fed from the bottle through the flexible plastic hose to a gun-type multi-dose hypodermic or drench syringe allowing adjustable volume dosages. Many animals are inoculated or treated with the same needle or drenching apparatus. The use of a container that holds many inoculations or treatments is beneficial because individual doses do not have to be prepared for each animal and the person administering the medication is free to move about without restriction.

During use, however, a vacuum is often developed in the system because it is typically air-tight and the semi-rigid plastic container does not collapse. As medication is removed from the container, a vacuum is created and the syringe tends to suck air into the container since the passage through the needle constitutes the only vent in the system. This is an undesirable result because it affects the subsequent amount of medication to be administered and makes it possible for air to be injected into the animal.

Notwithstanding indications to the contrary, it is common practice that after the last animal is inoculated or treated, the medication remaining in the system is dispensed back into the container for later use. If the remaining medication is not to be used for an extended period of time, the medication may be poured into another container and the plastic container rinsed and stored. There is typically little effort or concern expended with respect to sanitation, shelf-life expiry, contamination with previous contents, and cleanliness. It is common practice, notwithstanding indications to the contrary, to pour different medications in the container without cleansing the equipment, often causing contamination. This conventional method of inoculating or orally force medicating livestock presents a significant risk of injection abscesses and secondary infection, often resulting in death, impaired weight gain and poor meat quality.

SUMMARY OF THE INVENTION

The fluid dispensing apparatus of the present invention avoids the above-mentioned disadvantages and drawbacks which are characteristic of the prior art.

The fluid dispensing apparatus of the present invention comprises a flexible, collapsible fluid container and an adjustable volume, multi-dose fluid dispensing device. The adjustable volume, multi-dose fluid dispensing device is in fluid communication with the fluid container.

In preferred embodiments of the present invention, the fluid dispensing apparatus comprises additional elements that facilitate the convenience, ease of operation and cleanliness of the apparatus.

Numerous objects, features and advantages of the present invention will be readily apparent to those of ordinary skill in the art upon a reading of the following disclosure when taken in conjunction with the accompanying drawings.

DETAILED DESCRIPTION OF THE PREFERRED EMBODIMENTS

Figure 1:
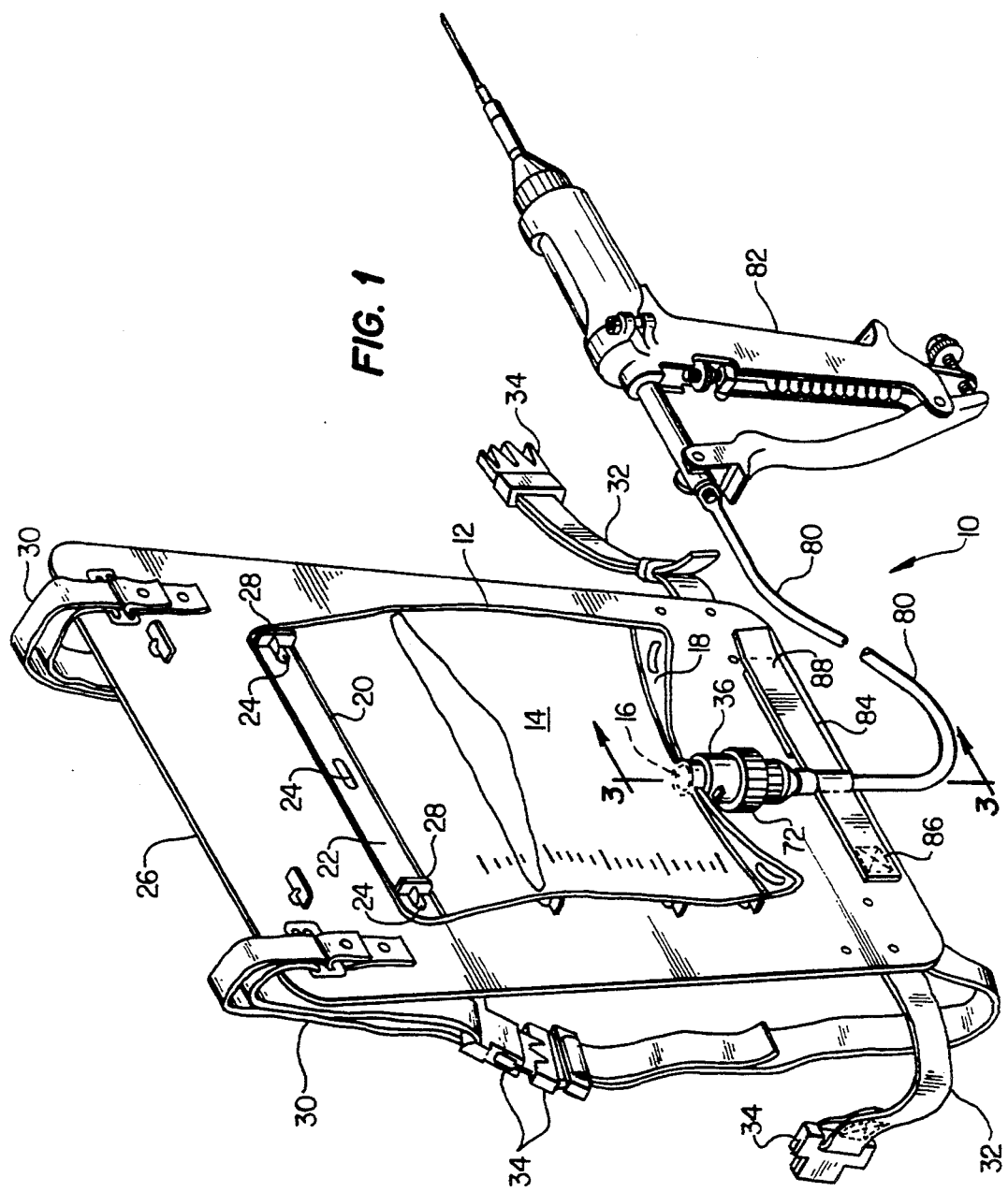
FIG. 1 is a perspective view of the fluid dispensing apparatus of the present invention.

Referring now to the drawings and particularly to FIG. 1, a fluid dispensing apparatus 10 includes a flexible, collapsible fluid container 12 which defines a body portion 14 that is sealed around the perimeter thereof except for a port 16. The container 12 includes a flattened portion 18 adjacent the port 16 and a flattened portion 22 at the end 20 opposite the port 16. The flattened portion 22 preferably includes a plurality of hanger holes 24 so that the container 12 may be hung in any suitable manner for convenient administration of oral or parenteral fluid or any other desired material.

As shown in FIG. 1, the fluid container 12 may be hung from a device such as a backpack 26 which includes clips 28, an adjustable shoulder harness 30, an adjustable waist belt 32 and buckle members 34. By means of the shoulder harness 30, the waist belt 32 and the buckle members 34, the backpack 26 may be adjusted to fit a user and provide convenient operation of the fluid dispensing apparatus 10. Those of ordinary skill in the art will recognize that more than one container 12 may be hung from backpack 26 and that any convenient means may be utilized to support container 12. Although not shown in FIG. 1, backpack 26 may include a protective flap that folds down and covers the fluid container 12.

The fluid container 12 is similar to conventional commercially available IV fluid bags. Preferably, the fluid container 12 is formed of two opposed pieces of die cut polyvinyl chloride material, most preferably medical grade USP 6 material, that are welded around their respective perimeters except for the location of the port 16. The fluid container 12 preferably is also made from polyvinyl chloride material that comprises a component that absorbs ultraviolet radiation to minimize the transmission of ultraviolet radiation to the contents of the fluid container 12. In this manner, the shelf-life effectiveness of photosensitive fluids may be prolonged. Such materials are commercially available such as from Delmed, Inc. of Ogden, Utah. As noted above, the fluid container 12 preferably is made of a flexible material that easily collapses upon itself to prevent the creation of a vacuum in the fluid dispensing apparatus 10 as the fluid contents are removed therefrom.

Figure 2:
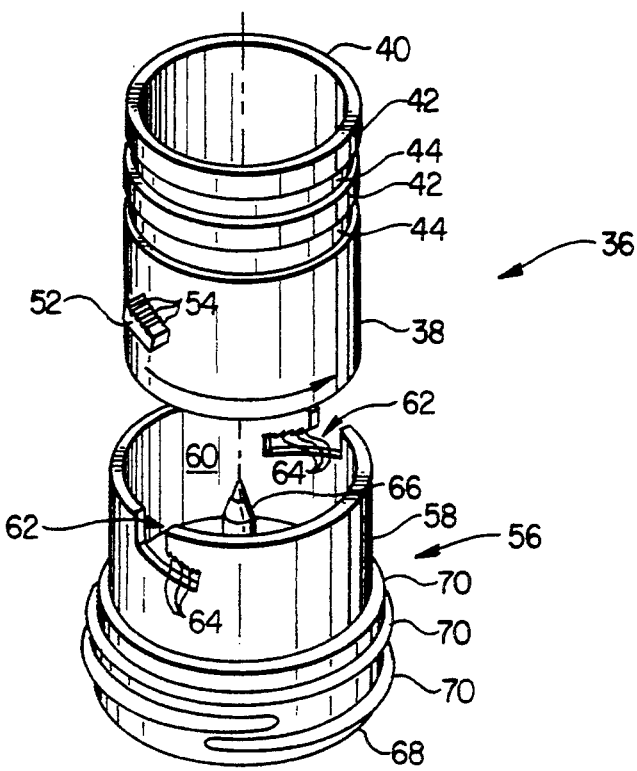
FIG. 2 is an exploded view of a portion of the fluid dispensing apparatus depicted in FIG. 1.

A neck member 36 is disposed within port 16 of the container 12. As shown in FIG. 2, the neck member 36 defines a body portion 38 having an outer diameter approximately equal to the inner diameter of the port 16 of fluid container 12. The neck member 36 is disposed and sealingly engaged within the port 16 of fluid container 12 to provide a fluid tight seal between the neck member 36 and the fluid container 12. The neck member 36 is sealingly engaged with the port 6, preferably by means of R. F. welding, dielectric sealing or heat crimping. Those of ordinary skill in the art will recognize that any suitable means may be utilized to engage the neck member 36 within the port 16 to provide a fluid tight seal therebetween.

The end 40 of neck member 36 that is disposed within port 16 preferably includes portions 42 having an outer diameter approximately equal to the outer diameter of the body portion 38 alternating with portions 44 having a smaller outer diameter than the outer diameter of body portion 38 to advantageously improve the fluid tight seal between neck member 36 and port 16. The neck member 36 preferably is injection molded by conventional techniques well known to those of ordinary skill in the art. Preferably, the neck member 36 is formed of polyvinylchloride material, most preferably medical grade USP 6 material.

Figure 3:
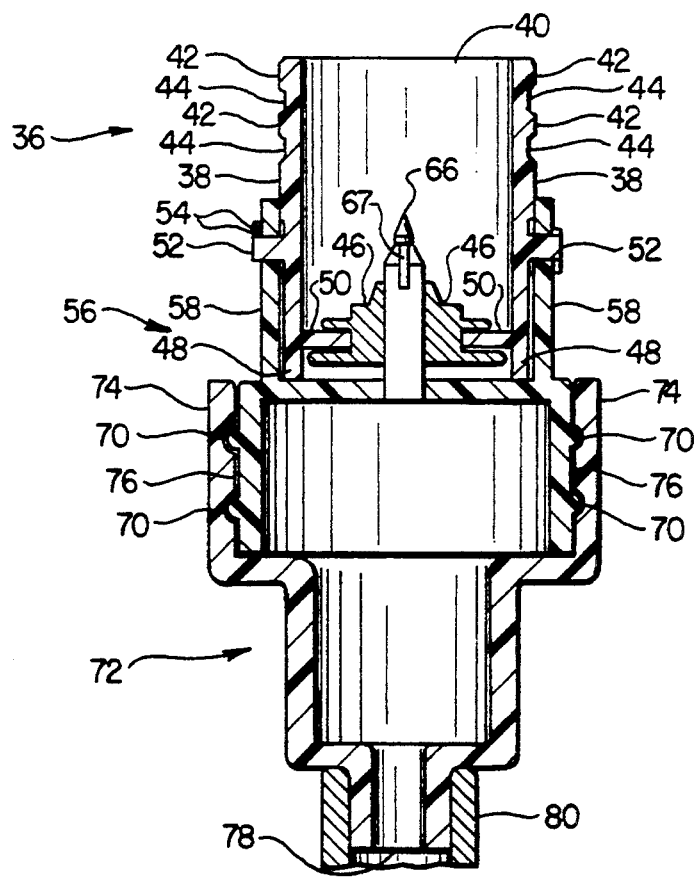
FIG. 3 is a section taken along line 3—3 of FIG. 1.

As shown in FIG. 3, a septum 46 is disposed within the end 48 of the neck member 36 opposite the portions 42 and 44 of alternating outer diameter. The septum 46 is received in sealing engagement by annular seat member 50 disposed adjacent end 48 of the neck member 36. The septum 46 is installed in neck member 36 after the container 12 is filled with a desired fluid to seal the fluid within the container 12. The septum 46 provides a resealable closure for the fluid container 12 and is of conventional construction such as those commercially available septums used presently in the medical field that when punctured by a lance form and maintain a fluid-tight seal about the lance and then reseal upon removal of the lance. Such septums are commercially available from Packaging West, Inc. of Denver, Colo. Preferably, the septum 46 is formed of a natural or synthetic rubber compound.

The neck member 36 includes diametrically opposed tabs 52 disposed on the outer surface thereof. The tabs 52 include a plurality of teeth 54, the purpose of which is discussed below.

As shown in FIGS. 2 and 3, an adapter 56 is engaged with neck member 36. The adapter 56 includes an annular body portion 58 defining a cavity 60. The annular body portion 58 has an inside diameter that is approximately equal to the outside diameter of the body portion 38 of neck 36. Thus, the adapter 56 longitudinally slidingly engages the neck member 36.

The body portion 58 of the adapter 56 includes diametrically opposed L-shaped slots 62 having a plurality of teeth 64. The width of the slots 62 is slightly larger than the width of the tabs 52 of neck member 36. Thus, when the adapter 56 longitudinally slidingly engages the neck 36, the tabs 52 of the neck member 36 are received within the slots 62. When the adapter 56 is rotated clockwise relative to the neck member 36, the teeth 54 engage the teeth 64 to prevent longitudinal adjustment between the adapter 56 and the neck member 36. It will be recognized by those of ordinary skill in the art that the adapter 56 can be disengaged from the neck 36 by disengaging the teeth 64 from the teeth 54 and rotating the adapter counterclockwise with respect to the neck 36.

Lance means 66 are disposed within the cavity 60 of the adapter 56. Lance means 66 comprises a hollow spike having one or more vents 67, preferably three vents 67. As shown in FIG. 3, when the adapter 56 longitudinally slidingly engages the neck 36, the lance means 66 punctures the septum 46 disposed in neck member 36 and projects into the fluid within the fluid container 12.

When the adapter 56 is disengaged from the neck member 36 and the lance means 66 is withdrawn from the septum 46, the septum 46 reseals in a conventional manner to prevent the escape of fluid from or contamination of fluid within the fluid container 12. The fluid container 12 may then be stored without leakage.

The adapter 56 preferably includes outer threads 70 at an end 68 opposite the slots 62. The purpose of outer threads 70 is discussed below.

The adapter 56 including the lance means 66 preferably is injection molded by conventional techniques well known to those of ordinary skill in the art. Preferably, the adapter 56 including the lance means 66 is formed of polypropylene.

A connector 72 is engaged with the adapter 56. The connector 72 defines a female end 74 having internal threads 76. The internal threads 76 of the connector 72 preferably threadedly engage the outer threads 70 of adapter 56. The connector 72 defines a nipple 78 opposite the female end 74.

One end of tubing 80 is engaged with nipple 78 of the connector 72. The other end of tubing 80 is connected to fluid dispensing means 82 as shown in FIG. 1. The fluid dispensing means 82 preferably comprises an adjustable volume multi-dose syringe such as the type disclosed in U.S. Pat. Nos. 2,074,401 and 4,033,346, the disclosures of which are incorporated herein by reference. The fluid dispensing means 82 may comprise a hypodermic needle or an oral administration device in a conventional manner well known to those of ordinary skill in the art for parenteral or oral administration of fluids.

The connector 72, tubing 80 and fluid dispensing means 82 are commercially available from N. J. Phillips Pty. Ltd. of Sydney, Australia. As shown in FIG. 1, backpack 26 preferably includes retaining means 84 which overlaps tubing 80 to hold tubing 80 against the backpack 26. The retaining means 84 is affixed to backpack 26 at a first end 86 such as by sewing or other conventional means well known to those of ordinary skill in the art. The retaining means 84 is releasably engaged with the backpack 26 at a second end 88 such as by Velcro ® or other conventional means well known to those of ordinary skill in the art.

In operation, the fluid container 12 is filled with a desired fluid. A septum 46 is sealingly engaged with seat member 50 of the neck member 36. If the fluid disposed within the fluid container 12 is not to be administered immediately, a dust cap (not shown) may be engaged with the neck member 36 to prevent the accumulation of dust on the septum 46. The dust cap (if present) preferably is formed of polypropylene.

When it is desired to dispense the fluid disposed within the fluid container 12, one end of tubing 80 is connected to the nipple 78 of the connector 72. The other end of the tubing 80 is connected to the fluid dispensing means 82. Next, the internal threads 76 at the female end 74 of the connector 72 are engaged with the outer threads 70 of the adapter 56. Then the dust cap (if present) is removed from the neck member 36 of the fluid container 12 and the adapter 56 is longitudinally slidingly engaged with neck member 36 by aligning the slots 62 of the adapter 56 with the tabs 52 of neck member 36, and rotating the adapter 56 relative to the neck member 36 until the teeth 64 of the adapter 56 engage the teeth 54 of the tabs 52.

When the adapter 56 is longitudinally slidingly engaged with neck member 36, the lance means 66 of the adapter 56 punctures the septum 46. Once the lance means 66 punctures the septum 46, the fluid dispensing means 82 is in fluid communication with the contents of the fluid container 12.

It is further contemplated that a fluid container 12 may be filled with a flushing, cleansing or sanitizing agent such as distilled water and attached to the tubing 80 and fluid dispensing means 82 after use. The flushing, cleansing or sanitizing agent may then be pumped through the system by repeated operation of the fluid dispensing means 82 thereby flushing, cleansing or sanitizing the entire system beyond the fluid container 12 before it is stored.

The benefits of the apparatus of the present invention begin with the nature of the fluid container 12. Because the fluid container 12 may be prefilled under sanitary conditions, the possibility of infection from the administered fluid is greatly reduced, if not eliminated. Furthermore, the fluid container 12 is disposable which will tend to minimize the reuse of the fluid container 12, minimize the mixing of drug ingredients, increase convenience, and minimize infection. Also, it will be much more difficult for a user to pump the fluid from the tubing 80 and the fluid dispensing means 82 back into the fluid container 12 after its final use. This will also contribute to more sanitary operations when compared to conventional techniques.

While the present invention has been described in detail and with reference to specific embodiments thereof, it will be apparent to one skilled in the art that various changes and modifications can be made therein without departing from the spirit and scope thereof.

What is claimed is:

1. A valve connection for controlling flow of a fluid, comprising:
    a) a first body having a longitudinal bore for receiving a fluid;
    b) a second body having a longitudinal bore for dispensing said fluid;
    c) means for releasably and sealingly connecting said first body to said second body to define a passage for the flow of said fluid from said first body to said second body through said bores; and
    d) valve means responsive to connection of said first body to said second body by said connection means for preventing the flow of said fluid when said first body and said second body are not connected and permitting the flow of said fluid when said first body and said second body are connected, said valve means comprising a septum securely disposed within one of said bodies and a hollow lance integrally connected within said other body;
    wherein said lance penetrates said septum upon connection of said first body to said second body; and
    wherein said lance is withdrawn from said septum and said septum remains disposed within said one of said bodies upon disconnection of said first body and said second body.

2. The valve connection of claim 1 wherein said connecting means comprises a plurality of tabs extending from one of said bodies for engagement in a plurality of corresponding slots formed in said other body.

3. The valve connection of claim 2 wherein said connecting means further comprises teeth correspondingly formed on said tabs and in said slots for releasably locking said tabs in said slots.

4. The valve connection of claim 1 wherein said lance comprises a hollow spike having at least one vent.

5. The valve connection of claim 4 wherein said hollow spike has three vents.

6. The valve connection of claim 1 wherein said septum is resealingly penetrable.

* * * * *

UNITED STATES PATENT AND TRADEMARK OFFICE
CERTIFICATE OF CORRECTION

PATENT NO.  : 5,425,528
DATED       : June 20, 1995
INVENTOR(S) : John R. Rains et al.

It is certified that error appears in the above-indentified patent and that said Letters Patent is hereby corrected as shown below:

Column 3, line 9, change "port 6" to -- port 16 --.

Signed and Sealed this

Nineteenth Day of September, 1995

Attest:

BRUCE LEHMAN

*Attesting Officer*    *Commissioner of Patents and Trademarks*